United States Patent [19]

Chekan

[11] Patent Number: 4,701,167
[45] Date of Patent: Oct. 20, 1987

[54] MULTI-DIMENSIONAL APPLICATOR

[75] Inventor: William J. Chekan, Beverly, Mass.

[73] Assignee: The Kendall Company, Boston, Mass.

[21] Appl. No.: 776,310

[22] Filed: Sep. 16, 1985

[51] Int. Cl.$^4$ .............................................. A61M 35/00
[52] U.S. Cl. ..................................... 604/310; 604/301
[58] Field of Search .................................. 128/200.23; 604/294–310

[56] References Cited

U.S. PATENT DOCUMENTS

| | | | |
|---|---|---|---|
| 889,810 | 6/1908 | Robinson | 604/310 X |
| 1,377,760 | 5/1921 | Dorment | 604/301 |
| 1,692,143 | 11/1928 | Strunz | 604/301 |
| 3,306,252 | 2/1967 | Knight et al. | 128/200.23 |

*Primary Examiner*—Dalton L. Truluck
*Attorney, Agent, or Firm*—Donald N. Halgren

[57] ABSTRACT

The present invention comprises an applicator for the discharge of disinfectant from an aerosol can. The applicator provides an inner and an outer confinement means which permits the discharge of disinfectant from the aerosol can onto a relatively large area being treated.

The applicator also comprises an inner confinement adapter which is disposed within the outer confinement means so as to permit a smaller portion of a patient's body to be disinfected. A finger may disposed against the inner confinement apparatus and disinfected appropriately due to the smaller size of the inner confinement means as opposed to the outer confinement means. The flow of disinfectant when the outer confinement means is utilized is not compromised because of the spaced relationship axially between the two confinement rims.

8 Claims, 4 Drawing Figures

MULTI-DIMENSIONAL APPLICATOR

BACKGROUND OF THE INVENTION (1) Field of the Invention

This invention relates to applicators for disinfectant aerosol spray bottles and more particularly to spray applicators on nozzles which are adapted for medical purposes.

(2) Prior Art

The medical field uses pressurized gases which propel a skin disinfectant such as isopropyl alcohol onto the skin of a patient prior to injection or puncture thereof.

The nozzle of a standard aerosol disinfectant unit comprises a generally cup-shaped applicator known as a pressure bell disposed on the discharge end of a pressurized can of disinfectant. The distal circular end of the applicator is placed against the patient's skin to form a closed chamber. The can of pressurized disinfectant is pressed against the patient to deliver a small dose of disinfectant thereon and the pressure facilitates penetration of the disinfectant into the skin. The disinfected area is thereby encircled by the applicator. The diameter of the rim of an applicator is of the order of about one inch. This is satisfactory dimensionally for disinfecting relatively flat areas of the body such as may be found on an arm, torso or a leg. This is unsatisfactory however, when the patient has a smaller extremity such as a finger which has to be disinfected prior to being punctured for a sampling of blood or an injection or the like.

Where the applicator known in the art cannot be used, such as on a finger, a cotton swab is usually moistened directly by pressure being applied thereto against the applicator can.

It is an object of the present invention to provide an applicator which is useful for larger portions of a patient's body as well as smaller portions, both of which may be disinfected by the same applicator on the spray end of a disinfectant can.

It is a further object of the present invention to provide a common applicator which will permit the use of a disinfectant without the need of the extra cotton swab which could promote infection elsewhere.

BRIEF SUMMARY OF THE INVENTION

The present invention comprises an applicator which mates with the discharge nozzle on a pressurized spray can. The applicator is of cup-shaped configuration having an outer ring which is implaceable against a generally flat portion of skin of a patient's body. The inner surface of the cup-shaped applicator is of generally hemispherical configuration, the center portion of which is in fluid communication with the discharge nozzle of the pressurized can. A second cup-shaped member is disposed concentrically within the outer cup-shaped member. The diameter of the inner cup is a fraction of the diameter of the outer cup. The diameter of the inner cup is of the order of about ¼ to ⅝ of an inch. The inner cup has an annular rim that defines a plane which is disposed away from (beneath) the plane of the rim of the outer cup, that is, disposed towards the nozzle.

When an applicator of the present invention is pressed against say, the skin of an arm or leg of a patient, wherein a large portion of skin is encirclable by the rim of the outer cup and thereby defines the area of the patient which is to be disinfected. The outer rim presses the skin away from the aerosol can to provide the proper skin tension and area thereof to be disinfected and it defines a closed chamber. When a smaller "flat" area, such as the pad portion of a finger of a patient is to be treated, that finger is placed across the smaller rim of the inner cup, the smaller rim then acting to encircle the smaller area to be disinfected.

Since the rim of the inner cup is within the confines of the outer cup and closer to the spray nozzle than the rim of the outer cup, it does not interfere with the flow of disinfectant to the outer cup as it is discharged from the nozzle of the applicator can. Further embodiments of the present invention may include the inner rim having perforations adjacent the periphery thereof to provide full circulation of the pressurized gas as it is discharged from the common orifice within the inner and outer cup.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
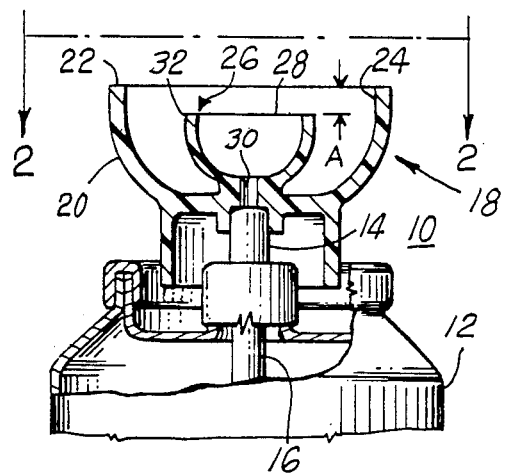
FIG. 1 is a partial side elevational view of a pressurizable can having an applicator thereon.

Referring now to the drawings in detail, and particularly to FIG. 1, there is shown a skin disinfectant means 10 comprising an aerosol spray can 12 having a standard pressure actuatable discharge nozzle 14 disposed on the distal end of the can 12. A fluid pick-up tube 16 may be arranged within the can 12 to direct fluid therein, through the nozzle 14 when that nozzle 14 has a force applied to it from outside the can 12. The disinfectant within the can 12 may be isopropyl alcohol or the like, pressurized by a propellant gas such as propane and or butane.

An applicator means 18 is shown disposed on top of the aerosol can 12, in FIG. 1. The applicator means 18 comprises an outer cup 20 having an annular rim 22 on its distal edge. The outer cup 20 may have a generally hemispherically shaped inner surface 24.

An inner applicator means 26 is disposed within the outer cup 20. In the preferred embodiment, the inner applicator means 26 comprises an inner cup 28 of generally hemispherical configuration. A discharge orifice 30 concentric to both the outer cup 20 and the inner applicator means 26, is disposed through the center of the inner applicator means 26, which orifice 30 is in fluid communication with the open distal end of the discharge nozzle 14. The inner cup 28 has an annular rim 32 on its distal edge, which rim 32 defines a plane that is a distance "A", or about one-eighth to about one-fourth of an inch closer toward the orifice 30, (beneath, as shown in the Figures) than is the plane defined by the rim 22 of the outer cup 20. The inside diameter of the rim 22 of the outer cup 20 may be in the range of about three-fourths of an inch to about one and one-fourth of an inch. The inside diameter of the rim 32 of the inner cup 28 may be in the range of about one-fourth of an inch to about five-eighths of an inch, which should be wide enough to spread across and define a closed chamber of an averaged size finger of a patient to whom it will be pressed.

Figure 2:
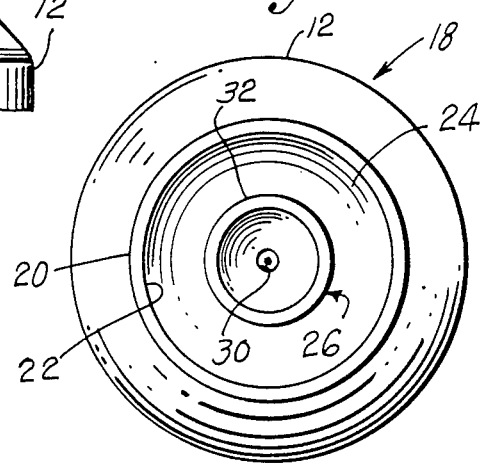
FIG. 2 is a view taken along the lines 2—2 of FIG. 1.

A plan view of the applicator means 18 is shown in FIG. 2, showing the concentric nature of the orifice 30 with the inner and outer rims 32 and 22.

Figure 3:
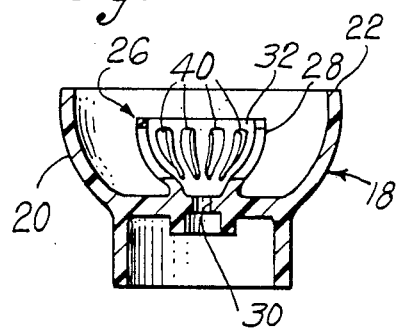
FIG. 3 is a side elevational view of the applicator in a further embodiment thereof.
Figure 4:
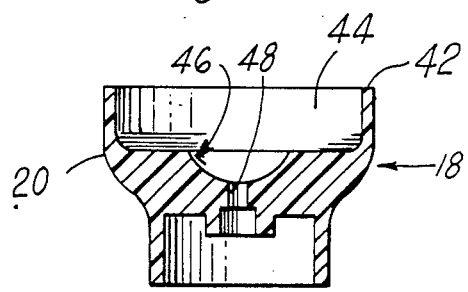
FIG. 4 is yet a further embodiment of that shown in FIG. 3.

A further embodiment of the applicator means 18 is shown in FIG. 3, which is similar to that shown in FIG. 1 except that the surface defining the cup 28 has a plurality of openings 40 therein. The openings 40 are arranged so as to help the flow of disinfectant between the inner cup 32 and the outer cup 20. Still a further embodiment is shown in FIG. 4 wherein the applicator 18 comprises an annular rim 42 having a generally cylindrically shaped inner surface 44. An inner applicator means 46 is arranged concentrically therewith having an orifice 48 which is in fluid communication with the discharge nozzle 14 of the aerosol can 12. The volume between the innermost applicator 46 and the outer periphery of the outer cup 20 may be of solid material, which material is preferably plastic. The inner surface of the innermost applicator 46 in this embodiment may be generally hemispherically shaped, as shown in FIG. 4.

Thus there has been shown an applicator means which permits a common applicator to be utilized on a discharge end of an aerosol spray can when disinfecting both a large portion of a patient's skin as well as a small portion of a patient's body such as a finger.

A combination applicator permits either skin area to be disinfected without the common hassle of using a cotton swab for the problem of changing the applicator itself if a particular portion of the patient's skin is to be disinfected.

I claim:

1. An applicator for facilitating discharge of disinfectant from an aerosol can, which applicator provides containment and delivery means for disinfectant against a finger of a patient or a larger area of a patient, comprising:

an outer confinement means; and
an inner confinement means disposed within said outer confinement means with an arrangement of orificii through the sides thereof for fluid communication therebetween, said inner confinement means having a distal peripheral surface which defines a plane disposed away from a plane defined by the outer confinement means.

2. An applicator as recited in claim 1, wherein said outer confinement means comprises a cup having a peripheral rim.

3. An applicator as recited in claim 2, wherein said inner confinement means comprises an inner cup having a peripheral rim.

4. An applicator as recited in claim 3, wherein a channel is disposed within said inner confinement means, which channel is fluidly communicable with a nozzle means on any aerosol can thereattached.

5. An applicator as recited in claim 3, wherein the space between said inner cup and said outer cup is solid.

6. An applicator as recited in claim 3, wherein said outer cup has an inner surface of generally hemispherical configuration.

7. An applicator as recited in claim 3, wherein said inner cup has an inner surface of generally hemispherical configuration.

8. An applicator as recited in claim 4, wherein said channel is in fluid communication with said inner cup and said outer cup.

* * * * *